United States Patent [19]

Strumpf et al.

[11] Patent Number: 4,954,495

[45] Date of Patent: Sep. 4, 1990

[54] FUNGICIDES AND PLANT-GROWTH CONTROLLING AGENTS

[75] Inventors: Thomas Strumpf, Potsdam; Horst Lyr, Eberswalde; Dieter Zanke, Potsdam-Babelsberg; Gerlinde Zollfrank nee Baumann, Potsdam, all of German Democratic Rep.; Gyula Oros; Ferenc Viranyi, both of Budapest, Hungary; Tibor Ersek, Columbia, Mo.

[73] Assignee: Chinoin Gyogyszer es Vegyeszeti Termekiek Gyara R.T., Budapest, Hungary

[21] Appl. No.: 344,009

[22] Filed: Apr. 26, 1989

Related U.S. Application Data

[63] Continuation-in-part of Ser. No. 835,608, Mar. 3, 1986.

[30] Foreign Application Priority Data

Mar. 4, 1985 [DE] Fed. Rep. of Germany ......... 273728

[51] Int. Cl.$^5$ .................... A01N 37/12; A01N 37/44; A01N 43/54
[52] U.S. Cl. .................................. 514/231.2; 514/539
[58] Field of Search ...................... 514/231.2, 534, 539

[56] References Cited

U.S. PATENT DOCUMENTS 4,032,657  6/1977  Moser ................................. 514/534

FOREIGN PATENT DOCUMENTS 0229297  7/1982  German Democratic Rep. ................... 514/231.2

OTHER PUBLICATIONS

CA 92:41601q, *Fungicidal Acylanilines*, Bosone et al., 1980.
CA 97:2148f, *Methyl N–Phenylacetyl–N–2,6–Xylyl Olinate (M9834), A New Systemic Fungicide Controlling Mildew*, 1982.
CA 105:166910h, *Fungicidal and Plant Growth Regulating Agents*, Strumpf et al., 1986.
CA 110:110114n, *Acylamide Containing Synergistic Fungicide Compositions*, Detre et al., 1989.

*Primary Examiner*—Allen J. Robinson
*Attorney, Agent, or Firm*—Herbert Dubno; Jonathan Myers

[57] ABSTRACT

Synergistic plant fungicides are disclosed which comprise Tridemorph and Benalaxyl in a synergistically effective weight ratio.

3 Claims, No Drawings

FUNGICIDES AND PLANT-GROWTH CONTROLLING AGENTS

CROSS REFERENCE TO RELATED APPLICATIONS

This application is a continuation-in-part of copending application Ser. No. 835,608 filed Mar. 3, 1986.

The invention relates to antifungal and plant-growth controlling compositions and to their application in plant-protection.

Alkylmorpholines are put into action to fight the true powdery mildew fungi (DE 11 64 152, DE 11 98 125, DD 140 412, DE 26 56 747). Acylanilines have found entrance as Oomycete-active fungicides into the practical plant-protection (see R. Wegler, Chemie der Pflanzenschutz und Schadlingsbekampfungsmittel, Vol. 6).

Based on the relatively narrow activity-spectrum of all these compounds different advantageous mixtures for morpholine fungicides (DD 134 040, DD 104 416, DD 111 014, DD 116 384, DD 121 013, DE 26 33 874, DE 27 07 709, DE 27 18 721, DE 28 35 253, DD 155 481, DD 157 592) and acylanilines too (EP 26 873, DE 30 21 068, GB 2 017 496, JP 82 128 609, EP 30 570, DE 33 01 281) became known.

Nevertheless for some applications the activity, intensity and the fungicide spectrum could be improved.

The object of the present invention is to find suitable combination-partners for morpholine-fungicides which lead to an increase of the fungicide activity, and inhibit the development of resistance and simultaneously control the fungal growth through intervention in the metabolism.

It was found, that a mixture consisting of a fungicide from the group of morpholines (A) N-tridecyl-2,6-dimethylmorpholine (Tridemorph) (1);
N-cyclododecyl-2,6-dimethylmorpholine (Dodemorph) (2);
N-alkyl($C_{12}$)-2,6-dimethylmorpholine (Aldimorph) (3);
4-(3-p-tert.-butylphenyl)-2-methylpropyl-2,6-cisdimethylmorpholine (Fenpropemorph) (4)
as well as their plantphysiologically acceptable salts, molecular-and addition compounds and one of the following fungicides (B)
N-(2,6-dimethylphenyl)-N-furoyl-(2)-alaninemethylester (Furalaxyl) (5);
N-(2,6-dimethylphenyl)-N-chloroacetyl-alaninemethylester (CGA 29 212) (6);
N-(2,6-dimethylphenyl)-N-phenylacetyl-alaninemethylester (Benalaxyl) (7);
2-chloro-N-(2,6-dimethylphenyl)-N-(tetrahydro-2-oxo-3-furanyl)-acetamide (Ofurace) (8);
3-chloro-N-(tetrahydro-2-oxo-3-furanyl)-cyclopropanecarboxanilide (Cyprofuram) (9);
2-methoxy-N-(2-oxo-1,3-oxazolidin-3-yl)-N-(2,6-dimethylphenyl)acetamide (Oxadixyl) (10);
N-isoxazol-5-yl-N-(2,6-xylyl)-alaninemethylester (LAB 149 202 F) (11);
N-(2,6-dimethylphenyl)-2-methoxy-N-(tetrahydro-2-oxo-3-furanyl)acetamide (RE 26 745) (12);
N-(2,6-dimethylphenyl)-2-methoxy-N-(tetrahydro-2-oxothien-3-yl)-acetamide (RE 26 940) (13),
as active ingredients, possesses an improved fungicide activity especially against Oomycetes and is suitable for the control of plant-growth. The effects induced by the combination of the active agents are based on synergistic influences. The increased practical breadth of application of the new combinations is advantageous, which makes it possible to control the downy and powdery mildews. Moreover the probability of the appearance of resistant strains, because of the different mode of action of the two components and the differences in sensitivity of the stages of fungal life cycle, markedly decreased. The mixtures according to the invention this way represent an enrichment of the prior art.

With the new combination the damaging fungi appearing on plants or on the parts of plants can be decreased. Based on the systemic properties of both components even new growing parts of plants will be protected against fungal attacks. The mixtures are efficacious against phytophathogenic fungi of the following groups: Ascomycetes (e.g. Erysiphe- and Sclerotinia-species), Oomycetes (firstly Phytophthora-, Peronospora- and Plasmopara-species) and Basidiomycetes (e.g. Rhizoetonia-species).

The combinations are employed advantageously for the control of plant-growth of cereals, vegetables and vegetable cultures as e.g. cucumbers, tomato, sun flowers, among others of cultivated plants as well as of some ornamental plants. At the employed concentrations no phytotoxic damage was observed. The seed corn's quality will not be affected disadvantageously. Further, the fungicidal effect of the components of the combinations is of importance for the safeguarding of the yield.

The mass ratio of the morpholine-fungicides and fungicides of the second group in the mixtures can be varied, between 20:1 to 1:2, especially from 20:1 to 1:1, advantageously from 10:1 to 2:1, preferred from 5:1 to 3:1.

The preparation of the enumerated morpholines (A) inclusive of its salts, molecular and addition compounds (DE 11 64 152, DE 11 73 722, DE 24 61 513, DE 11 98 125, DD 140 041, DE 26 56 747), as well as of the other known fungicides (B) (DE 25 13 788, DE 23 50 944, DD 142 042, US 3 933 860, DE 27 24 786, FR 2 463 132, EP 26 873, DE 28 41 824, BE 871 668) is well known.

The combinations of the active ingredients according to the invention can be transferred into usual formulations as solutions, emulsion concentrates, suspensions, powders, spray powders, strewing powders, pastes, granulates, aerosols, seed corn powder etc. The formulations will include the active ingredients and can include surface active agents, solid or liquid diluents or solvents, liquefied gases under pressure and other materials as required to produce the desired formulation. The formulations are prepared by methods known per se.

Liquid solvents can be e.g.: fractions of mineral oils with a mean to high boiling point, e.g. kerosine or Diesel-oil, oils of plant or animal origin, aliphatic, cyclic and aromatic hydrocarbons, e.g. toluene, xylene, alkylated naphthalenes, cyclohexanes, paraffin, alcohols, glycols, esters, ketones and halogenated hydrocarbons, e.g. butanol, ethyleneglycol, methylethylketone, cyclohexanone, chloroform, chlorobenzene or polar solvents, e.g. dimethyl-formamide, dimethylsulfoxide or N-methylpyrrolidone.

As liquefied gases under pressure aerosol gases are meant e.g. halogenated hydrocarbons, propane, butane and carbon dioxide. As solid carriers natural rock flours, e.g. kaoline, talc, silica, montmorillonite and diatomaceous earth and synthetic rock flours, e.g. highly dispersed silicic acid, aluminum-oxide and silicates can be applied. For granulates the following materials are suitable as carriers: broken natural stones, e.g.

calcite, marble, pumice-stone, dolomite, synthetic granulates from inorganic and organic flours as well as granulates from organic material, e.g. sawdusts, shells of coconut, corn-cobs and tobacco stems.

The surface-active agents act as wetting emulsifying and/or dispersing agents. Here the following compounds can be taken into consideration: alkali-, earth alkali- and ammonium salts of ligninsulphonic acid, naphthalene-sulphonic acid, phenolsulphonic acid, alkylarylsulphonates, alkylsulphates, alkylsulphonates, alkali- and earth alkali salts of dibutylnaphthalene-sulphonic-acid, laurylethersulphate, fatty alcohol sulphates, alkali- and earth alkali salts of fatty acids, salts of sulphated hexadecanols, heptadecanols, octadecanols, salts of sulphated fatty alcohol glycolethers, condensation products of sulphonated naphthalenes and naphthalene derivatives with formaldehyde, condensation products of naphthalenes of naphthalenesulphonic acids respectively with phenol and formaldehyde, polyoxyethylene-octyl-phenolether, ethoxylated isooctylphenol, octylphenol, nonylphenol, alkylphenolpolyglycolether, tributylphenylpolyglycolether, alkylarylpolyether alcohols, isotridecyl alcohol, fatty alcohol ethyleneoxide-condensates, ethoxylated Rizinus-oil, polyoxyethylenealkylether, ethoxylated polyoxypropylene, laurylalcoholpolyglycolether-acetal, sorbitester, lignin, sulphite waste alkalis and methyl cellulose.

The formulations may further contain adhesion agents as carboxy methylcellulose, natural or polymers as gum arabic, polyvinylalcohol or polyvinylacetate and the like.

The formulations contain generally 1 to 95% by weight of the active ingredients (A)+(B).

Aqueous forms of application can be prepared from emulsion concentrates, suspensions, spray powders (strewing powders) etc. by addition of water. The preparation of emulsions or oil dispersions is carried out by dissolving the active ingredients and other additives in oil or a solvent or homogenization in water by means of wetting, dispersing- or emulsifying agents.

The application takes place in the usual manner, e.g by immersion, pouring, spraying, strewing or dusting. The applied quantities depend on the specific goal of application and generally lie between 0.5 and 5.0 kg/ha respectively 10–200 g active ingredient per 100 kg seed corn. The active agent combinations according to the invention can be mixed for the enlargement of the application breadth and plant protection with other known fungicides, herbicides, insecticides, desiccants, defoliants, growth controlling agents or fertilizers.

BRIEF DESCRIPTION OF THE DRAWING

The sole FIGURE is a graph which plots the percentage of fungal growth inhibition against varying proportions of Benalaxyl and Tridemorph.

EXAMPLE 1

Composition of a sprinkling powder
18 weight % of Tridemorph
7 weight % of LAB 149 202 F
5 weight % of calciumligninsulphonate
5 weight % of alkylphenol-ethyleneoxide addition agent
20 weight % of silicic acid
45 weight % of kaolin

EXAMPLE 2

Composition of an emulsion-concentrate 35 weight % of Aldimorph
15 weight % Ofurace
18.5 weight % toluene
18.5 weight % cyclohexanone
10 weight % of tert. butanol
2 weight % epoxydated octylphenolether
1 weight % Tween 20 ... 80

EXAMPLE 3

Synergistic effect of mixtures from morpholine-fungicides (A) and fungicides (B) on Phytophthora cinnamomi in vitro Phytphthora cinnamomi was grown in Petri dishes on green pea agar media containing the mentioned active agents, combinations respectively in the given concentrations. The inoculation was carried out with mycelial discs. After 5 days of cultivation at 21° C. the colony diameter was measured and the inhibition of the radial growth related to the untreated control was calculated. The synergistic effect was calculated according to COLBY.

| Active Agent, combination resp. | Concentration (mg/l) | Growth-inhibition (%) | Effect according to COLBY (%) |
| --- | --- | --- | --- |
| Tridemorph (1) | 4 | 51 | — |
|  | 0.4 | 6 | — |
|  | 0.04 | 1 | — |
| Dodemorph (2) | 40 | 52 | — |
|  | 4 | 12 | — |
|  | 0.4 | 2 | — |
| Aldimorph (3) | 40 | 64 | — |
|  | 4 | 1 | — |
|  | 0.4 | 1 | — |
| Aldimorph HCl (3a) | 40 | 81 | — |
|  | 4 | 24 | — |
|  | 0.4 | 3 | — |
| Fenpropemorph HCl (4a) | 4 | 1 | — |
|  | 0.4 | 1 | — |
| Fenpropemorph-methosulphate (4b) | 0.4 | 3 | — |
|  | 0.04 | 2 | — |
| Furalaxyl (5) | 1 | 69 | — |
|  | 0.1 | 19 | — |
|  | 0.01 | 2 | — |
| Benalaxyl (7) | 10 | 40 | — |
|  | 1 | 19 | — |
|  | 0.1 | 6 | — |
| Ofurace (8) | 10 | 56 | — |
|  | 1 | 20 | — |
|  | 0.1 | 5 | — |
| Cyprofuram (9) | 10 | 68 | — |
|  | 1 | 14 | — |
|  | 0.1 | 1 | — |
| LAB 149 202 F (11) | 10 | 84 | — |
|  | 1 | 25 | — |
|  | 0.1 | 2 | — |
| Re 26 745 (12) | 1 | 77 | — |
|  | 0.1 | 12 | — |
|  | 0.01 | 2 | — |

EXAMPLE 4

Synergistic curative effect of mixtures from morpholine (A) and acylalanine (B) fungicides on Plasmopara halstedii downy mildew of sunflower Sunflower germs (Helianthus annus cv. GK-70) were infected with a suspension of zoospores of Plasmopara halstedii ($2.5 \times 10^5$ cell/ml). After 24 hours the seedlings were immersed into the aqueous solutions (emulsions) of various concentrations of the mentioned substances (from 50 EC) for 18 hours.

After 14 days the percent ratio of the infected plants was determined and the $ED_{50}$ value was calculated. The significance for a synergistic effect was expressed as Co T.I. and calculated according to the following equation:

$$Co\ T.I. = \frac{\frac{1}{ED_{50}\ Mixt}}{\frac{a}{ED_{50}\ A} + \frac{b}{ED_{50}\ B}}$$

In this equation a and b indicate the current weight parts of the active agents A and B in the mixture. A Co T.I. value >1.25 means, that a significant synergism was present.

| Active agent resp. combination | $ED_{50}$ (mg/l) | Co. T.I. |
|---|---|---|
| Aldimorph (3) | 1040.0[x/] | — |
| Aldimorph HCL (3a) | 771.0[x/] | — |
| RE 26745 (12) | 33.0 | — |
| 3 + 12 (3 + 1) | 5.4 | 5.57 |
| 3a + 12 (3 + 1) | 16.1 | 1.82 |

[x/] phytotoxic

EXAMPLE 5

Synergistic effect of mixtures from morpholine (A) and acylalanine (B) fungicides on the vegetative growth of some Phytophthora species in vitro The fungi were—as described in Example 3—grown on green-pea agar plates containing the active ingredients. The $ED_{50}$ values were calculated based on the inhibition of the radial growth compared to the untreated control. The mixing ratio in all of the cases was 4:1 weight parts. The synergistic effect was expressed as CO T.I. according to Example 4, where values from 1.0±0.25 mean an additive effect, and those from >1.25 a significant synergistic effect.

| Combination | P. cactorum $ED_{50}$ (Co T.I.) (mg/l) | P. cambivora $ED_{50}$ (Co T.I.) (mg/l) |
|---|---|---|
| Tridemorph (1) | 24.2 | 12.4 |
| Dodemorph (2) | 47.3 | 258.0 |
| Aldimorph (3) | 32.7 | 36.2 |
| Aldimorph HCl (3a) | 34.6 | 23.6 |
| Fenpropemorph (4) | 175.0 | 6.41 |
| Furalaxyl (5) | 0.17 | 0.05 |
| Benalaxyl (7) | 1.8 | 0.25 |
| Ofurace (8) | 0.79 | 1.12 |
| Cyprofuram (9) | 5.0 | 2.8 |
| Oxadixyl (10) | 0.12 | 0.45 |
| LAB 149 202 F (11) | 0.15 | 0.08 |
| RE 26 940 (13) | 0.22 | 0.31 |
| 1 + 10 | 0.19 (0.62) | 0.10 (3.93) |
| 1 + 11 | 0.09 (1.63) | 0.73 (0.11) |
| 2 + 10 | 0.02 (5.94) | 0.09 (4.97) |
| 3 + 5 | 0.11 (1.51) | 0.07 (0.71) |
| 3 + 7 | 1.22 (1.21) | — — |
| 3 + 8 | 1.37 (0.53) | 0.75 (1.33) |
| 3 + 9 | 2.3 (1.35) | 2.4 (0.89) |
| 3a + 9 | 1.4 (2.26) | 0.91 (2.09) |
| 3a + 13 | 0.27 (0.80) | — — |
| 4 + 10 | 0.02 (5.98) | 0.22 (1.60) |

EXAMPLE 6

Inhibition of the epicotyl longation of soy-bean Glycine max by mixtures from morpholine (A) and acylalanine (B) fungicides (immersion of the seed)

Soy-bean seeds c.v. (Harosoy) were dressed with the agents in the given quantity of application and one week after treatment they were sown (50 seeds of each application). After three weeks the length of epicotyl was measured.

| Active agent combination | Concentration (g/100 kg of seeds) | Length of the epicotyles (mm) | Difference comp. to the control (mm) | Effect according to COLBY |
|---|---|---|---|---|
| untreated control | — | 147 | — | — |
| Tridemorph-methosulphate | 40 | 122 | −25 | — |
| Fenpropemorph methosulphate (4b) | 40 | 39 | −108 | — |
| Benalaxyl (7) | 10 | 151 | +4 | — |
| LAB 149 202 F (11) | 10 | 140 | −7 | — |
| RE 26 745 (12) | 10 | 155 | +8 | — |
| 1b + 11 | 40 + 10 | 86 | −61 | 31 |
| 1b + 12 | 40 + 10 | 111 | −36 | 21 |
| 4b + 7 | 40 + 10 | 32 | −115 | 15 |
| 4b + 12 | 40 + 10 | 18 | −129 | 38 |

EXAMPLE 7

Growth control of tomato-plants Solanum lycopersicum by mixtures of morpholine (A) and acylalanine (B) fungicides The enumerated active agents were formulated one by one and in combination as 25 WP, suspended in water and sprayed run off on tomato plants (c.v. Harzfeuer) in the four-leaf stage (20 plants in each application). After cultivation for 12 days in a green-house the dry-weight was determined and compared with that of the untreated control.

| Active agent, combination resp | conc. (mg/l) | dry-weight (g) | increase of the dry-weight (%) |
|---|---|---|---|
| Untreated control | 0 | 1.36 | 100 |
| Tridemorph (1) | 0.1 | 1.48 | 109 (—) |
| Tridemorph HCl (1a) | 0.1 | 1.56 | 115 (—) |
| Aldimorph (3) | 0.1 | 1.51 | 111 (—) |
| Aldimorph HCl (3a) | 0.1 | 1.53 | 112 (—) |
| Fenpropemorph (4) | 0.1 | 1.53 | 112 (—) |
| Fenpropemorph HCl (4a) | 0.1 | 1.50 | 110 (—) |

EXAMPLE 8

Joint action of morpholine (tridemorph) and phenylamide (benalaxyl) fungicides on the zoospore release of *Pseudoperonospora cubensis* (Berk. et Curt) Rostow.

P. cubensis (Oomycetes, Peronosporales, Peronosporaceae) is an obligate parisitic fungus, causative agent of destructive disease of cucurbitaceous plants. Like other peronosporaceous fungi (downy mildews) and Phytophthoras, this pathogen also spreads through the air by zoosporangia.

The experiments were carried out with zoosporangia of *P.cubensis* collected in a greenhouse from the infected cucumber plants. The examination was carried out according to the methods described in OROS. G. and VIRANYI, F. (1986: Acta Phytopathologica et Entomologica Hungarica, 21: 157–164). The efficacy Was expressed as the percent of inhibition.

RESULTS

| No. | Treatment Substances | Concentration mg/l | Inhibition Rate (%) | -MRV |
|---|---|---|---|---|
| 1. | Tridemorph | 100 | 69 | |
| 2. | Tridemorph | 500 | 93 | |
| 3. | Benalaxyl | 100 | 61 | |
| 4. | Benalaxyl | 500 | 97 | |
| 5. | Benalaxyl + Tridemorph | 20 / 80 } 100 | 92 | 23 |
| 6. | Benalaxyl + Tridemorph | 100 / 400 } 500 | 100 | 3 |

$LSD_{5\%} = 2.5$
MRV = Maximum response value according to Horsfall's model for demonstration of synergistic interaction.

CONCLUSION

Tridemorph and benalaxyl synergistically interact in the inhibition of asexual spores of *P. cubensis*, a peronosporaceous fungus.

EXAMPLE 9

Joint action of morpholine (tridemorph) and phenylamide (benalaxyl) fungicides on the vegetative growth of Phytophthora spp. (Oomycetes, Peronosporales, Pythiaceae).

*Phytopthora parasitica* f. sp. nicotianae var. tomato and *P. citricola* both are facultatively parasitic fungi able to infect their hosts either with mycelia or with zoosporangia (soil borne and air borne infections, respectively) causing serious loss of the yield before or after the harvesting.

The inhibition of vegetative growth of both fungi was tested. The efficacy was expressed in the percent of inhibition.

RESULTS

| No. | Substance | Treatment Conc. mg/L | Inhibition of the growth of P. citricola -MRV | P. parasitica -MRV |
|---|---|---|---|---|
| 1. | Tridemorph | 1 | 0 | 3 |
| 2. | " | 5 | 14 | 9 |
| 3. | " | 10 | 27 | 14 |
| 4. | " | 50 | 75 | 32 |
| 5. | " | 100 | 93 | 40 |
| 6. | Benalaxyl | 0.5 | 13 | 17 |
| 7. | " | 1 | 17 | 22 |
| 8. | " | 5 | 44 | 40 |
| 9. | " | 10 | 64 | 60 |
| 10. | " | 50 | 92 | 90 |
| 11. | " | 100 | 97 | 98 |

CONCLUSION

Tridemorph and Benalaxyl synergistically interact in the inhibition of the vegetative growth of Phytophthoras.

EXAMPLE 10

The effect of benalaxyl, tridemorph and their combination on the vegetative growth of *Phytophthora citricola* (Peronosporales)

The fungus was grown in 9 cm Petri dishes on green pea agar medium at a standard incubation temperature of 18°-20° C. in the darkness. Cultural techniques and assessments were made according to ROOKE, D. M. and SHATTOCK, R. C. (1983): J. Gen. Microbiol., 129:3401–3410.

The inhibition of radial growth was calculated in % as compared to the untreated control.

| Active agent, combination, resp. | Concentr. mg/l | Results: Inhibition of radial growth % | Synergistic effect % |
|---|---|---|---|
| 1. Tridemorph | 5 | 14 | |
| 2. Benalaxyl | 5 | 44 | |
| 3. 1 + 2 (4:1) | 5 | 74 | +30 |

EXAMPLE 11

Comparative study of antifungal activity of tridemorph, benalaxyl and their mixtures against sunflower downy mildew (SDM).

The sunflower cultivar, GK-70, highly susceptible to sunflower downy mildew and a metalaxyl-sensitive isolate of Plasmopara halstedii [Farlow] Berlese et de Toni (Oomycetes, Peronosporales) originating from field collection and maintained in the glasshouse on seedlings of sunflower were used throughout this study, according to OROS & VIRANYI (1987): Ann appl. Biol., 110:53–63.

Fungicide treatments

The germlings infected as described above were maintained in the glasshouse under the same conditions for 6 days after planting, and then sprayed run off with fungicides and Assessment of fungicidal efficacy:

The seedlings 2 days after treatment were transferred overnight (approximately 14–18 h) to a humid chamber at 18°-20° C. This induced sporulation of the fungus. To determine the intensity of sporulation, a 0–4 scale was used where the proportion of cotyledon area covered by zoosporangiophores was graded as follows: 0, no sporulation; 1–4, sporulation appearing on $<\frac{1}{4}$, $\frac{1}{4}-\frac{3}{4}$, $\frac{3}{4}-<4/4$ and $4/4$ of the totally cotyledon area, respectively and SDM infection rate was calculated by using McKinney's formula. Inhibition of sporulation was calculated as a percentage of the untreated control. Methods other than detailed here are described elsewhere (OROS & VIRANYI (1987): Ann appl. Biol., 110:53–63.

The significance of differences were proved either by F- or t- distributions according to G. M. CLARKE (1980): Statistics and Experimental Design, 2nd Edition, Edward Arnold (Publishers) Ltd. London, P=5% was chosen as a limit of accepted probability. Three different models were used for evaluating the character of interaction:

(A) COLBY's model compares the efficacy of a particular fungicide combination to the least effect calculated from the efficacies of each single fungicide component applied alone.

(B) HORSFALL's model makes a comparison between the effect of a combination and that of the most effective single component used alone at the same mass part (dosage rate).

(C) Comparison to the most potent treatment: All treatments within an experiment are compared to the most effective one and those are considered to be of equal value that show no significant difference by any accepted data analysis system at usual level of significance (P=<10% for field experiments. P=<5% for glasshouse and laboratory (in vitro) experiments.

Table of Example 11

Demonstration of joint action against sunflower downy mildew of the mixtures from benalaxyl and tridemorph.

(Comparing the experimental models for revealing synergetic action for curative treatment.)

TABLE of Example 11

| No. | Compounds Mixtures Respectively | Conc. mg/l | Inhibitory effect % | Models for Comparison | | |
|---|---|---|---|---|---|---|
| | | | | A | B | C |
| 1. | Benalaxyl | 1.0 | 0 | — | — | −33.0 |
| 2. | Benalaxyl | 2.0 | 9.5$^a$ | — | — | −32.0 |
| 3. | Benalaxyl | 3.0 | 12.0$^{ab}$ | — | — | −22.0 |
| 4. | Benalaxyl | 5.0 | 15.0$^{bc}$ | — | — | −19.0 |
| 5. | Benalaxyl | 7.0 | 19.0 | — | — | −14.0 |
| 6. | Benalaxyl | 10.0 | 20.5 | — | = | −11.0 |
| 7. | Tridemorph | 10.0 | 0 | — | −20.5 | −34.0 |
| 8. | Benalaxyl + Tridemorph | 1.0 9.0 | 9.0$^a$ | +9.0* | −11.5 | −25.0 |
| 9. | Benalaxyl + Tridemorph | 2.0 8.0 | 20.5 | +11.0* | = | −11.0 |
| 10. | Benalaxyl + Tridemorph | 3.0 7.0 | 27.5$^a$ | +15.5* | 7.0* | −6.5 |
| 11. | Benalaxyl + Tridemorph | 4.0 6.0 | 31.5 | +18.0* | +11.0* | −2.5* |
| 12. | Benalaxyl + Tridemorph | 5.0 5.0 | 34.0 | +19.0* | +13.5* | = |
| 13. | Benalaxyl + Tridemorph | 6.0 4.0 | 28.0$^a$ | +11.0* | +7.5* | −6.0* |
| 14. | Benalaxyl + Tridemorph | 7.0 3.0 | 18.0 | −1.0 | −1.5* | −16.0 |
| 15. | Benalaxyl + Tridemorph | 9.0 1.0 | 20.0 | −0.5 | −0.5* | −14.0 |

$^+$ = The values of efficacy (% of inhibition) labeled by the same letter are not different significantly: LSD$_{5\%}$ = 4.3 (F = 21.4 > F=$F_{0.001}$ = 7.8), for benalaxyl; LSD$_{5\%}$ = 2.3 (F = 53.9 > F=$F_{0.001}$ = 17.8), for benalaxyl with tridemorph.
$^{++}$ = For comparing differences in SDM response to various treatments the COLBY's model (A), the relation to both maximum response value (B) and most potent treatment (C) were used. The values labeled by asterics, as a result of increased efficacy due to mixing tridemorph with benalaxyl, are not significantly different within the same column (P<5%).

EXAMPLE 12

Comparative study of antifungal activity of tridemorph, benalaxyl and their mixtures against root rot of pea.

The pea seeds (Pisum sativum L. cv. Rhone dwarf) were dressed with fungicides and 6 days behind were sowed to the soil infested with Pythium spp. The efficacy of treatments was evaluated 14 days after appearance of the first seedlings. The number of healthy plant individuals was counted and the proportion (%) calculated.

The efficacy of treatments was calculated as follows:

$$\text{Efficacy (\%)} = \frac{100 \times (100 - X_{ij})}{(100 - K)}$$

where $X_{ij}$ and K are the proportion of healthy plants in the i$^{th}$ treatment with j$^{th}$ fungicide and that of the untreated control, respectively.

| No. | Treatments Compounds, combinations | Dosage mg/kg | Efficacy % | −MRV |
|---|---|---|---|---|
| 1. | Tridemorph | 1000 | 0 | — |
| 2. | Benalaxyl | 1000 | 67 | — |
| | | 500 | 44 | — |
| | | 250 | 17 | — |
| | | 125 | 0 | — |
| 3. | 1 + 2 (4:1) | 1000 | 100 | +33 |
| | | 500 | 98 | +54 |
| | | 250 | 44 | +27 |
| 4. | 1 + 2 (7:3) | 1000 | 100 | +33 |
| | | 500 | 100 | +56 |
| | | 250 | 56 | +39 |

MRV = Maximum Response Value

EXAMPLE 13

The efficacy of seed treatments against downy mildew of soybean (Peronospora manshurica)

The seeds of soybean (Glycine max L. cv Harosoy) were dressed and sowen by the usual way. The efficacy was checked at two leaf stage (for infection rate) and after harvesting (for yield). The rate of use was 350 g of active substance per 100 kg of seed in each case.

| No. | Treatments (ratio) | Inhibition % | Yield t/ha | (+%) |
|---|---|---|---|---|
| 1. | Control | — | 0.990 | — |
| 2. | Metalaxyl$^a$ | 80 | 1.142 | (15.4) |
| 3. | Tridemorph$^a$ | — | 0.975 | (−1.5) |
| 4. | Benalaxyl$^a$ | 43 | 1.005 | (1.5) |
| 5. | 3 + 4 (3:1)$^b$ | 92 | 1.195 | (20.7) |
| 6. | 3 + 4 (4:1)$^b$ | 87 | 1.138 | (14.9) |

$^a$ = The commercial for Apron 35 sd (metalaxyl), Calixin 75 ec (tridemorph) and Galben 25 wp (benalaxyl) were applied.
$^b$ = The ratio of active ingredients (w/w) is concerned.

EXAMPLE 14

Synergistic effect of tridemorph and benalaxyl against Phytophthora infestans (in vitro)

Phytophthora infestans was grown in Petri dishes on green pea agar (GPA) media and discs of 7 mm in diameter were cut out of the edge of one weak old colony. These were put onto the surface of GPA media plates containing active ingredients at appropriate concentrations and kept there 6 days. Then the inocula were transferred onto GPA media free from fungicides (one disc per plate) and the residual activity was characterized by the retardation (%) of radial growth as compared to the untreated control.

The character of interaction was evaluated according to HORSFALL's model.

| No. | Treatment Compounds combinations | Dose | Inhibition % | −MRV |
|---|---|---|---|---|
| 1. | Tridemorph | 50 — | 33 | — |
| 2. | Benalaxyl | 50 | 49 | — |
| 3. | Tridemorph + Benalaxyl | 40 +10=50 | 100 | +51% |

MRV = Maximum Response Value

What is claimed is:

1. A fungicidal composition effective against Plasmopora halstedii which comprises a synergistic effective amount of:
   (a) Tridemorph; and
   (b) Benalaxyl;
in a weight ratio of substantially 5:1 to substantially 1:1; together with a fungicidally acceptable inert carrier.

2. The fungicidal composition defined in claim 1 wherein the weight ratio of the Tridemorph to the Benalaxyl is 5:1 to 3:1.

3. A fungicidal composition effective against Pythium species selected from the group consisting of Phytophthora citricola, phytophthora infestans, Phytophthora parasitica, Peronospora manshurica, and Pseudoperonospora cubensis, which comprises a synergistic effective amount of:
   (a) Tridemorph; and
   (b) Benalaxyl
in a weight ratio of substantially 5:1 to substantially 1:1; together with a fungicidally acceptable inert carrier.

* * * * *